United States Patent
Luo

(10) Patent No.: US 11,279,873 B2
(45) Date of Patent: Mar. 22, 2022

(54) THERMALLY ACTIVATED DELAYED FLUORESCENT AND SYNTHESIZING METHOD THEREOF

(71) Applicant: WUHAN CHINA STAR OPTOELECTRONICS SEMICONDUCTOR DISPLAY TECHNOLOGY CO., LTD., Wuhan (CN)

(72) Inventor: Jiajia Luo, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 512 days.

(21) Appl. No.: 16/337,463

(22) PCT Filed: Nov. 1, 2018

(86) PCT No.: PCT/CN2018/113270
§ 371 (c)(1),
(2) Date: Mar. 28, 2019

(87) PCT Pub. No.: WO2020/015245
PCT Pub. Date: Jan. 23, 2020

(65) Prior Publication Data
US 2021/0363416 A1    Nov. 25, 2021

(30) Foreign Application Priority Data
Jul. 18, 2018    (CN) .......................... 201810787840.5

(51) Int. Cl.
*C09K 11/06* (2006.01)
*C07D 401/12* (2006.01)

(52) U.S. Cl.
CPC ............ *C09K 11/06* (2013.01); *C07D 401/12* (2013.01); *C09K 2211/1022* (2013.01)

(58) Field of Classification Search
CPC ............................................. C09K 2211/1022
See application file for complete search history.

(56) References Cited

U.S. PATENT DOCUMENTS

2015/0141642 A1   5/2015  Adachi et al.
2019/0036035 A1   1/2019  Yang et al.

FOREIGN PATENT DOCUMENTS

CN    104271701 A    1/2015
CN    105038764 A    11/2015
CN    105585577 A    5/2016

OTHER PUBLICATIONS

Host Engineering for High Quantum Efficiency Blue and White Fluorescent Organic Light-Emitting Diodes.

*Primary Examiner* — Peter F Godenschwager
(74) *Attorney, Agent, or Firm* — JMB Davis Ben-David

(57) ABSTRACT

A thermally activated delayed fluorescent material and a synthesizing method thereof are provided. The thermally activated delayed fluorescent material has a structural formula as follows:

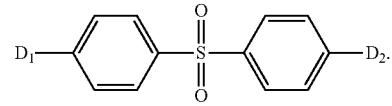

The synthesizing method has steps of: performing a heat treatment to a mixture of 4-bromo-4'-iodo-diphenyl sulfone, a first reactant, and a first catalyst to obtain a first reaction solution; performing a separating treatment on the first reaction solution to obtain a first intermediate; performing a (Continued)

heat treatment to a mixture of the first intermediate, a second reactant, and a second catalyst to obtain a second reaction solution; and treating the second reaction solution to obtain the thermally activated delayed fluorescent agent.

16 Claims, 2 Drawing Sheets

THERMALLY ACTIVATED DELAYED FLUORESCENT AND SYNTHESIZING METHOD THEREOF

CROSS-REFERENCE TO RELATED APPLICATIONS

This is the U.S. National Stage of International Patent Application No. PCT/CN2018/113270, filed Nov. 1, 2018, and which in turn claims the benefit of China Patent Application No. 201810787840.5, filed Jul. 18, 2018.

FIELD OF DISCLOSURE

The present disclosure relates to organic light emitting materials, and more particularly to a thermally activated delayed fluorescent material and a synthesizing method thereof.

BACKGROUND OF DISCLOSURE

At present, organic light-emitting diodes (OLEDs) displays have attracted much attention due to their advantages of being self-luminous, high luminous efficiency, large viewing angles, fast response times, low driving voltage, and thinness. In OLED light-emitting devices, it is critical to have a light-emitting guest material play a leading role. A light-emitting guest material, used in early OLEDs, is a fluorescent material. Because of a 1:3 ratio of singlet state to triplet state excitons in the OLED, a theoretical internal quantum efficiency (IQE) of the OLED based on fluorescent materials can only reach 25%, which greatly limits application of fluorescent electroluminescent devices. Heavy metal complex phosphorescent materials can utilize singlet state and triplet state excitons simultaneously due to a spin-orbit coupling of heavy atoms, resulting in a quantum efficiency of 100%. However, the heavy metals commonly used are precious metals such as Ir and Pt, and heavy metal complex phosphorescent materials in terms of blue light materials still need to be broken.

Thermally activated delayed fluorescence (TADF) materials, through clever molecular design, allow molecules to have a relatively small minimum singlet-triplet level difference. Thus, the triplet state excitons can be returned to the singlet state by reverse intersystem crossing, and then illuminate by the radiation transition to the ground state, so that the singlet state and triplet state excitons can be simultaneously utilized, and the quantum efficiency can achieve 100%. For TADF materials, fast reverse intersystem crossing constants and high photoluminescence quantum yields are necessary for a preparation of high efficiency OLEDs. At present, TADF materials with the above conditions are still relatively scarce compared to heavy metal Ir complexes. In a deep blue light field where phosphorescent heavy metal materials are to be broken, the TADF materials are further scarce.

From above, the quantum efficiency of the conventional OLED luminescent materials is low, resulting in low luminous efficiency of the OLED.

SUMMARY OF DISCLOSURE

The present disclosure provides a thermally activated delayed fluorescent material, so as to solve a problem of low luminous efficiency of the conventional OLED.

In order to solve the above problem, technical solutions provided by the present disclosure is as follows:

The present disclosure provides a synthesizing method of a thermally activated delayed fluorescent material. The thermally activated delayed fluorescent material has a structural formula as follows:

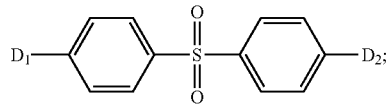

wherein $D_1$ is selected from one of following functional groups:

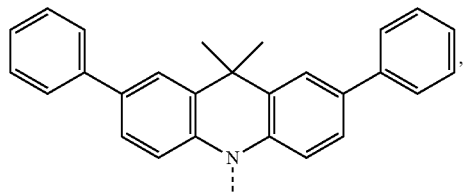

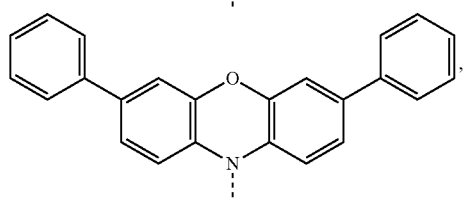

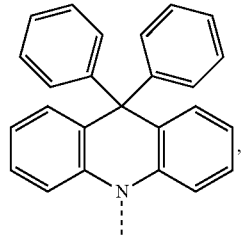

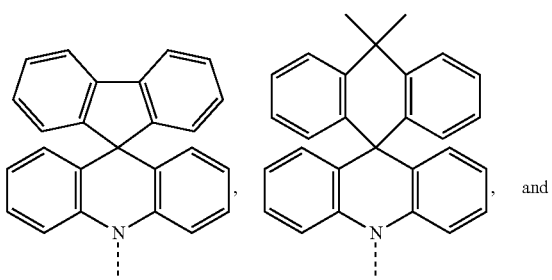

, and

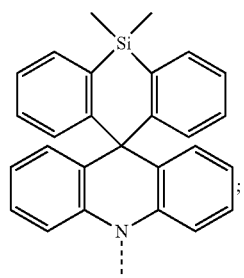

;

wherein $D_2$ is selected from one of following functional groups:

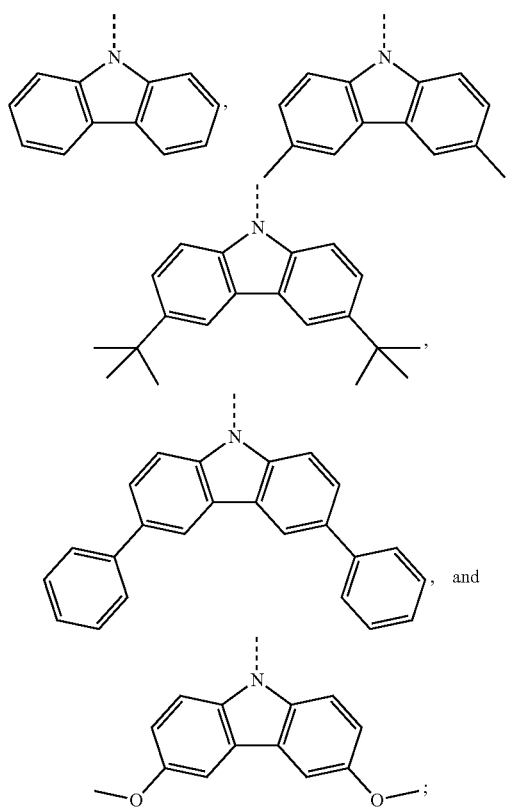

and the synthesizing method includes:

a step S10 of adding 4-bromo-4'-iodo-diphenyl sulfone, a first reactant, and a first catalyst to a first container, and performing a first heat treatment to obtain a first reaction solution, wherein the first catalyst is a mixture of cesium carbonate, cuprous iodide, 18-crown-6 ether, and N,N'-dimethylpropylene urea;

a step S20 of performing a separating treatment on the first reaction solution to obtain a first intermediate;

a step S30 of adding the first intermediate, a second reactant, and a second catalyst to a second container, and performing a second heat treatment to obtain a second reaction solution, wherein the second catalyst is a mixture of palladium acetate, tri-tert-butylphosphine tetrafluoroborate, and toluene; and a step S40 of treating the second reaction solution to obtain the thermally activated delayed fluorescent agent.

In at least one embodiment of the present disclosure, the first reactant is selected from one of following organic compounds:

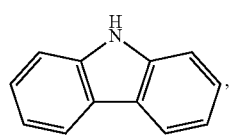

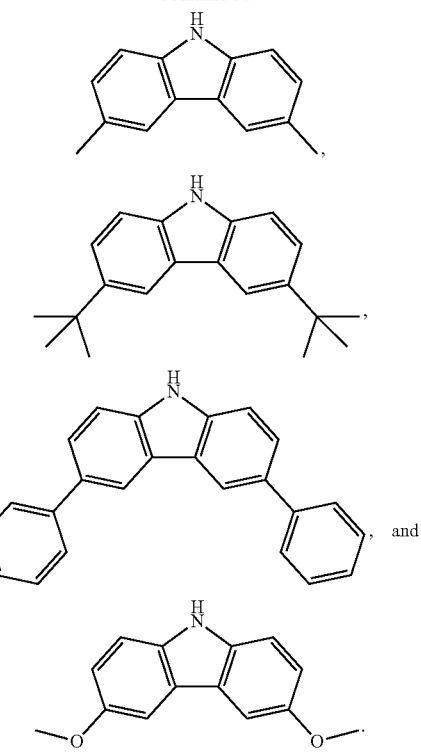

In at least one embodiment of the present disclosure, the second reactant is selected from one of following organic compounds:

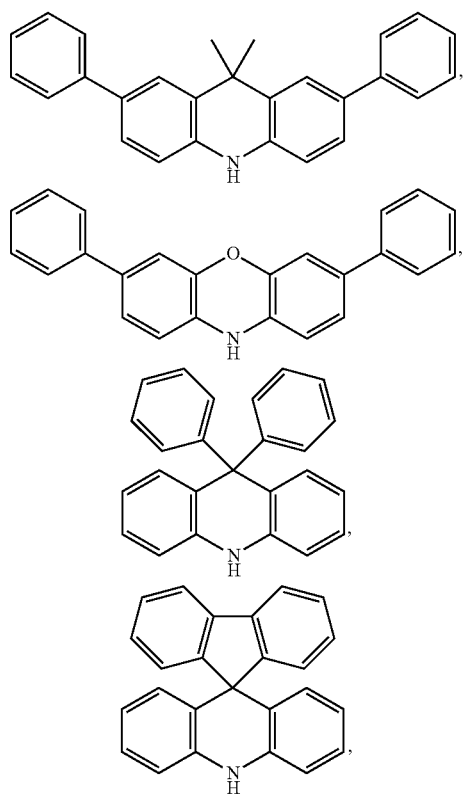

-continued

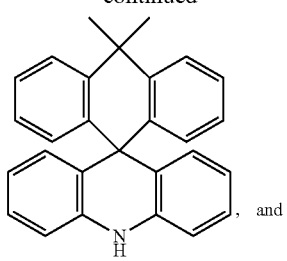, and

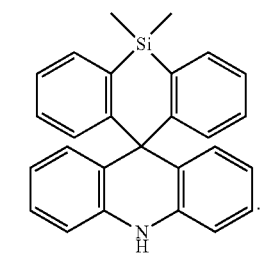.

In at least one embodiment of the present disclosure, the step S10 includes:
- a step S101 of adding 4-bromo-4'-iodo-diphenyl sulfone, the first reactant, cesium carbonate, cuprous iodide, and 18-crown-6 ether to the first container;
- a step S102 of vacuuming the first container three times and introducing nitrogen or an inert gas into the first container; and
- a step S103 of adding the N,N'-dimethylpropylene urea to the first container, and performing the first heat treatment to obtain the first reaction solution.

In at least one embodiment of the present disclosure, a temperature of the first heat treatment is 180° C., and a time of the first heat treatment is 24 hours.

In at least one embodiment of the present disclosure, the step S30 includes:
- a step 301 of adding the first intermediate, the second reactant, palladium acetate, and tri-tert-butylphosphine tetrafluoroborate to the second container; and
- a step 302 of placing the second container in a glove box filled with nitrogen or an inert gas, adding sodium tert-butoxide, then adding the toluene to the second container, and performing the second heat treatment to obtain the second reaction solution.

In at least one embodiment of the present disclosure, a temperature of the second heat treatment is 110° C., and a time of the second heat treatment is 24 hours.

The present disclosure further provides a thermally activated delayed fluorescent material comprising a structural formula as follows:

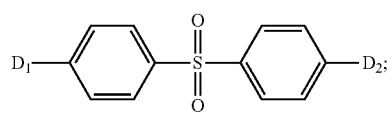

wherein $D_1$ is selected from one of following functional groups:

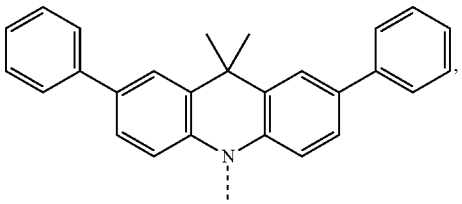;

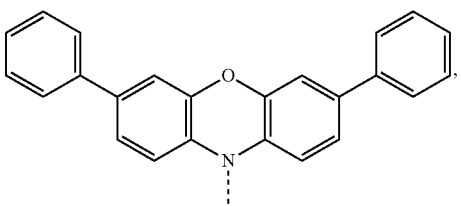;

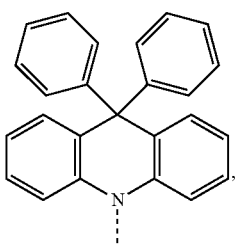;

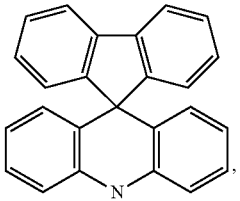;

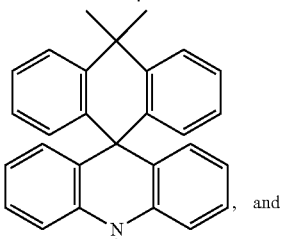, and

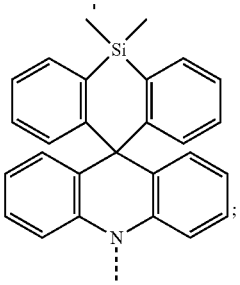;

and
wherein $D_2$ is selected from one of following functional groups:

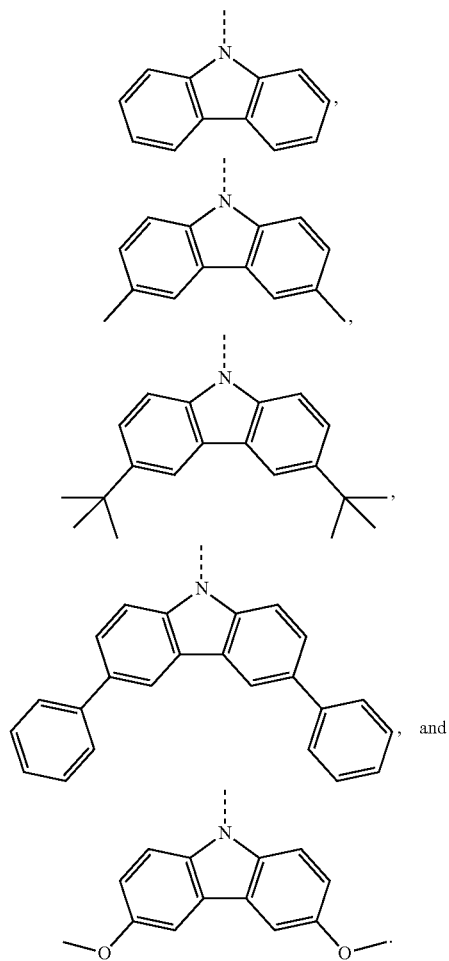

The present disclosure provides another synthesizing method of a thermally activated delayed fluorescent material. The thermally activated delayed fluorescent material has a structural formula as follows:

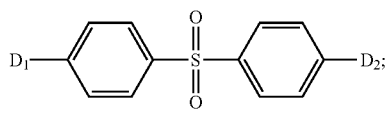

wherein $D_1$ is selected from one of following functional groups:

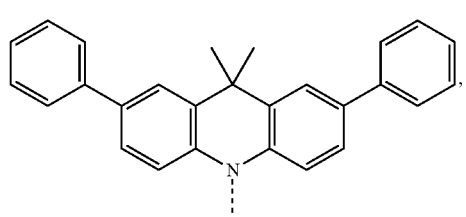

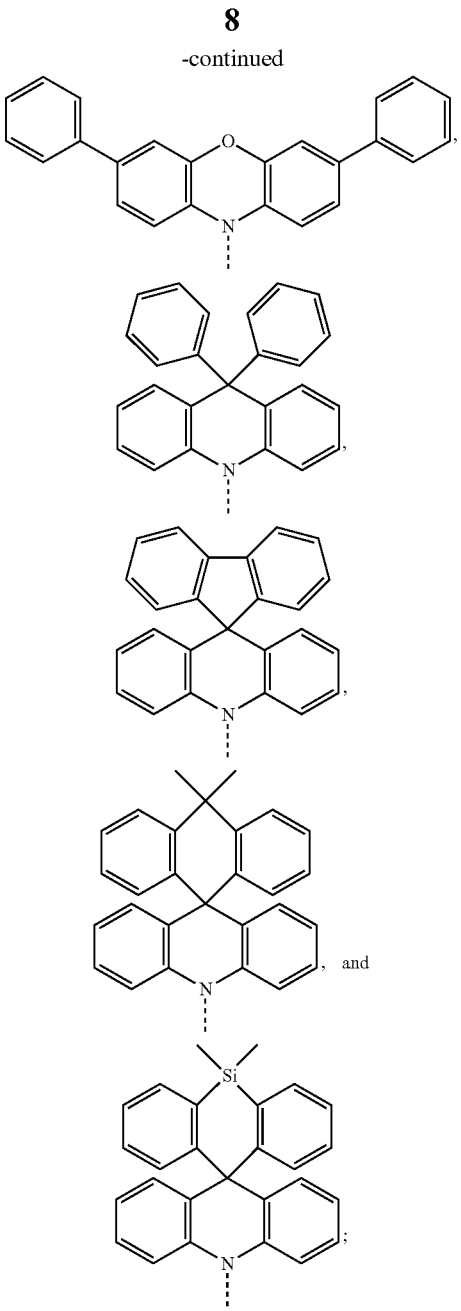

wherein $D_2$ is selected from one of following functional groups:

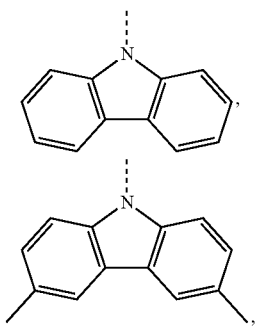

-continued

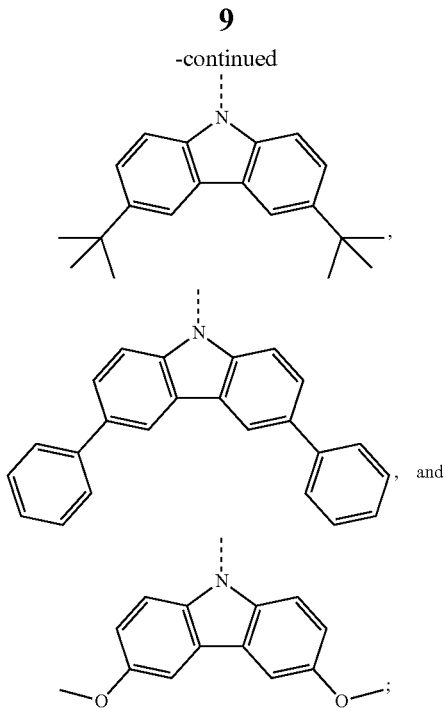, and and the synthesizing method comprises:
- a step S10 of adding 4-bromo-4'-iodo-diphenyl sulfone, a first reactant, and a first catalyst to a first container, and performing a first heat treatment to obtain a first reaction solution;
- a step S20 of performing a separating treatment on the first reaction solution to obtain a first intermediate;
- a step S30 of adding the first intermediate, a second reactant, and a second catalyst to a second container, and performing a second heat treatment to obtain a second reaction solution; and a step S40 of treating the second reaction solution to obtain the thermally activated delayed fluorescent agent.

In at least one embodiment of the present disclosure, the first reactant is selected from one of following organic compounds:

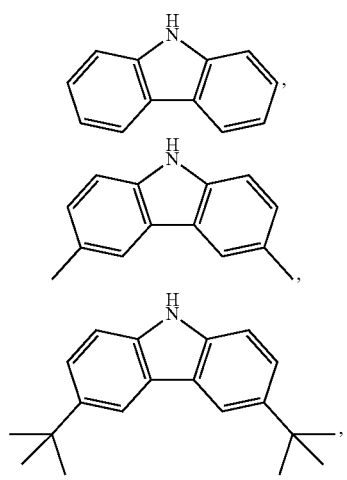

-continued

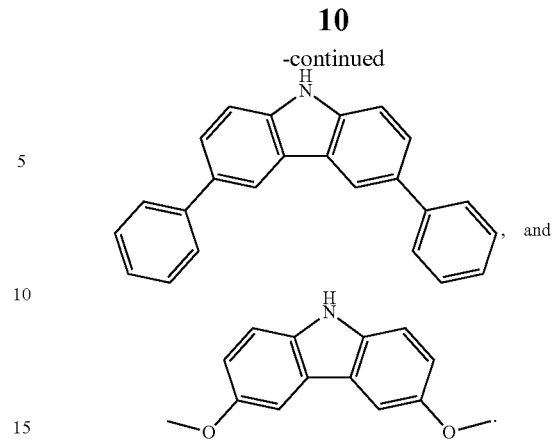, and

In at least one embodiment of the present disclosure, the second reactant is selected from one of following organic compounds:

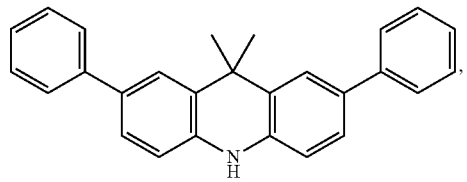,

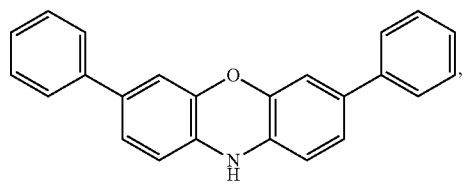,

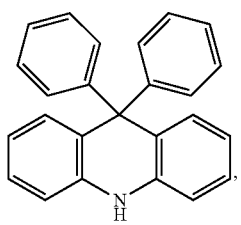,

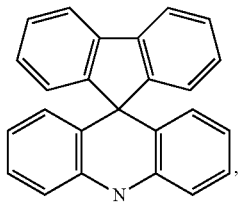,

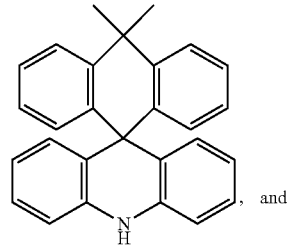, and

-continued

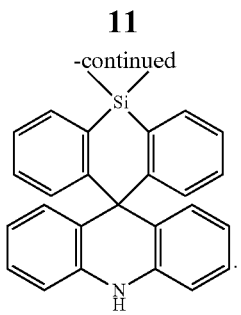

In at least one embodiment of the present disclosure, the first catalyst is a mixture of cesium carbonate, cuprous iodide, 18-crown-6 ether, and N,N'-dimethylpropylene urea.

In at least one embodiment of the present disclosure, the step S10 includes:
- a step S101 of adding 4-bromo-4'-iodo-diphenyl sulfone, the first reactant, cesium carbonate, cuprous iodide, and 18-crown-6 ether to the first container;
- a step S102 of vacuuming the first container three times and introducing nitrogen or an inert gas into the first container; and
- a step S103 of adding the N,N'-dimethylpropylene urea to the first container, and performing the first heat treatment to obtain the first reaction solution.

In at least one embodiment of the present disclosure, a temperature of the first heat treatment is 180° C., and a time of the first heat treatment is 24 hours.

In at least one embodiment of the present disclosure, the second catalyst is a mixture of palladium acetate, tri-tert-butylphosphine tetrafluoroborate, and toluene.

In at least one embodiment of the present disclosure, the step S30 includes:
- a step 301 of adding the first intermediate, the second reactant, palladium acetate, and tri-tert-butylphosphine tetrafluoroborate to the second container; and
- a step 302 of placing the second container in a glove box filled with nitrogen or an inert gas, adding sodium tert-butoxide, then adding the toluene to the second container, and performing the second heat treatment to obtain the second reaction solution.

In at least one embodiment of the present disclosure, a temperature of the second heat treatment is 110° C., and a time of the second heat treatment is 24 hours.

Beneficial effects of the present disclosure are that: the present disclosure synthesizes a thermally activated delayed fluorescent material with excellent luminescent properties by a combination of different functional groups, and improves a luminous efficiency of an OLED light-emitting device.

DESCRIPTION OF DRAWINGS

In order to more clearly describe embodiments of the present disclosure or technical solutions in a conventional technology, drawings required to be used for the embodiments or descriptions of the conventional technology are simply described hereinafter. Apparently, the drawings described below only illustrate some embodiments of the present disclosure. Those skilled in the art can obtain other drawings based on these drawings disclosed herein without creative effort.

DETAILED DESCRIPTION OF PREFERRED EMBODIMENTS

The following description of the embodiments with reference to the appended drawings is used for illustrating specific embodiments which may be used for carrying out the present disclosure. The directional terms described by the present disclosure, such as "upper", "lower", "front", "back", "left", "right", "inner", "outer", "side", etc. are only directions by referring to the accompanying drawings. Thus, the used directional terms are used to describe and understand the present disclosure, but the present disclosure is not limited thereto. In figures, elements with similar structures are indicated with the same numbers.

The disclosure is directed to the technical problems due to a quantum efficiency of the conventional thermally activated delayed fluorescent material being low, and a light emitting efficiency of the OLED being therefore low, so as to affect displaying. The present embodiment can solve the drawbacks.

The present disclosure provides a thermally activated delayed fluorescent material. The thermally activated delayed fluorescent material has a structural formula as follows:

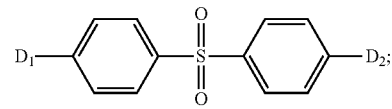

wherein $D_1$ is selected from one of following functional groups:

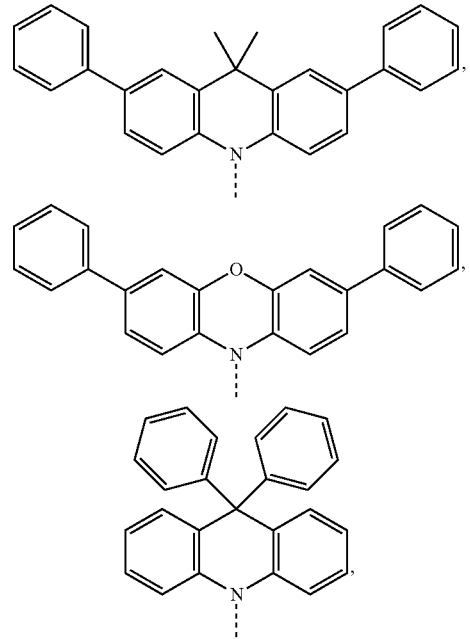

13
-continued

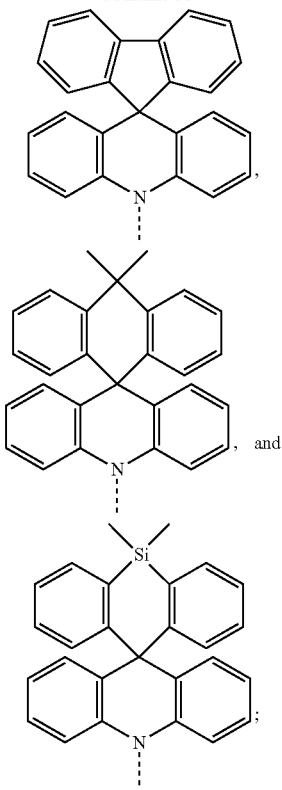
, and

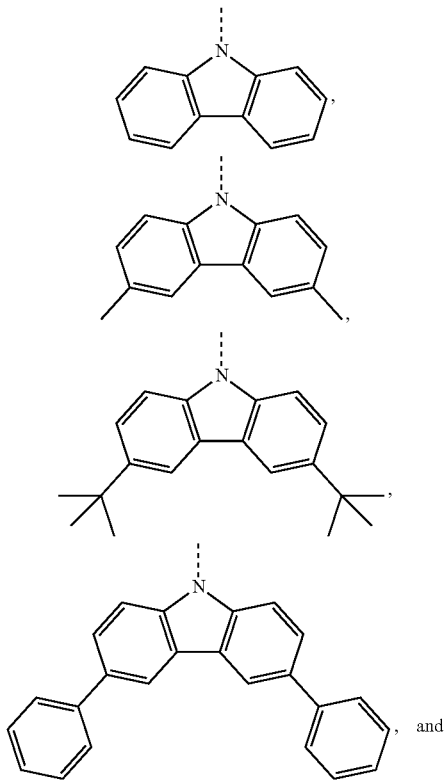
;

wherein D₂ is carbazole or carbazole derivatives, which is selected from one of following functional groups:

14
-continued

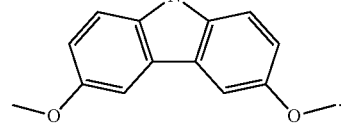

Figure 1:
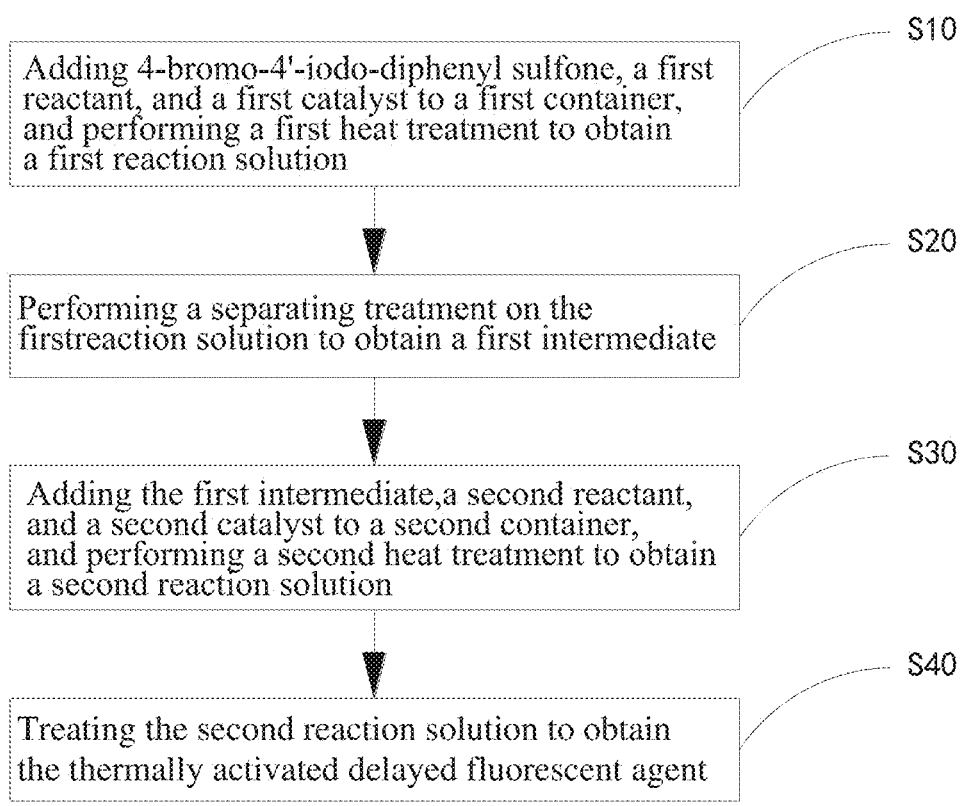
FIG. 1 is a flow chart showing steps of a synthesizing method of a thermally activated delayed fluorescent material of the present disclosure.

As shown in FIG. 1, the present disclosure further provides the synthesizing method of the above thermally activated delayed fluorescent material, comprising:

a step S10 of adding 4-bromo-4'-iodo-diphenyl sulfone, a first reactant, and a first catalyst to a first container, and performing a first heat treatment to obtain a first reaction solution;

a step S20 of performing a separating treatment on the first reaction solution to obtain a first intermediate;

a step S30 of adding the first intermediate, a second reactant, and a second catalyst to a second container, and performing a second heat treatment to obtain a second reaction solution; and a step S40 of treating the second reaction solution to obtain the thermally activated delayed fluorescent agent.

The first reactant corresponds to D₂ in the structural formula of the thermally activated delayed fluorescent material. The first reactant is selected from one of following organic compounds:

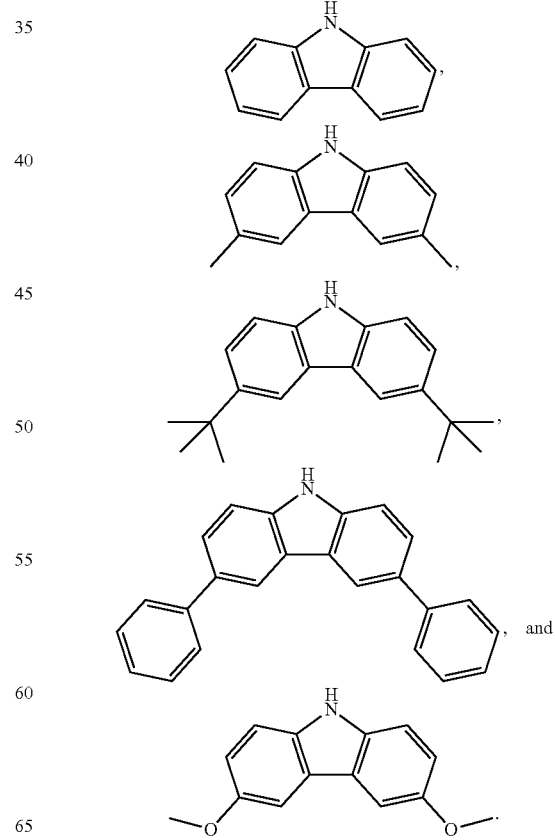

The second reactant corresponds to $D_1$ in the structural formula of the thermally activated delayed fluorescent material. The second reactant is selected from one of following organic compounds:

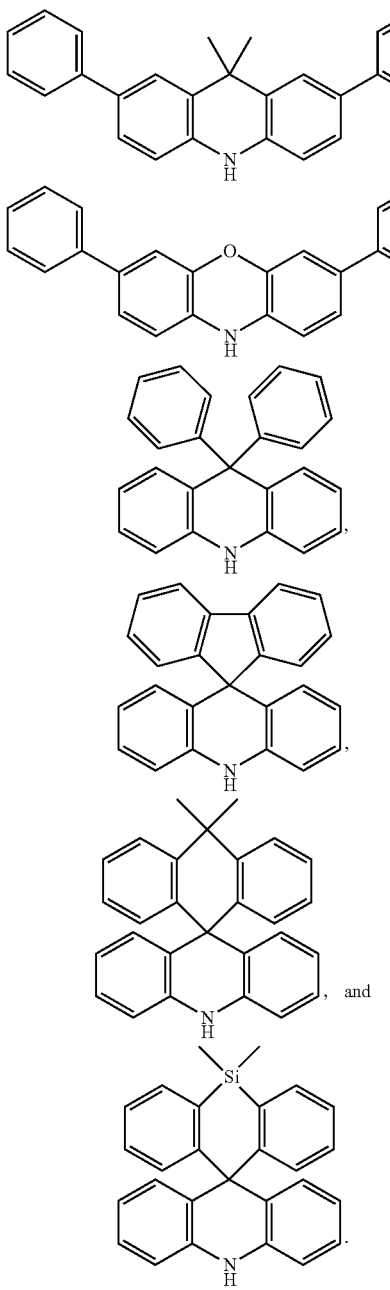

, and

The first catalyst is a mixture of cesium carbonate, cuprous iodide, 18-crown-6 ether, and N,N'-dimethylpropylene urea.

The step S10 includes:

a step S101 of adding 4-bromo-4'-iodo-diphenyl sulfone, the first reactant, cesium carbonate, cuprous iodide, and 18-crown-6 ether to the first container;

a step S102 of vacuuming the first container three times and introducing nitrogen or an inert gas into the first container; and a step S103 of adding the N,N'-dimethylpropylene urea to the first container, and performing the first heat treatment to obtain the first reaction solution.

A temperature of the first heat treatment is 180° C., and a time of the first heat treatment is 24 hours.

The second catalyst is a mixture of palladium acetate, tri-tert-butylphosphine tetrafluoroborate, and toluene.

The step S30 further includes:

a step 301 of adding the first intermediate, the second reactant, palladium acetate, and tri-tert-butylphosphine tetrafluoroborate to the second container; and a step 302 of placing the second container in a glove box filled with nitrogen or an inert gas, adding sodium tert-butoxide, then adding the toluene to the second container, and performing the second heat treatment to obtain the second reaction solution.

A temperature of the second heat treatment is 110° C., and a time of the second heat treatment is 24 hours.

The following description will be made in conjunction with specific embodiments.

Embodiment 1

A chemical structural formula of the thermally activated delayed fluorescent material in the present preferred embodiment is:

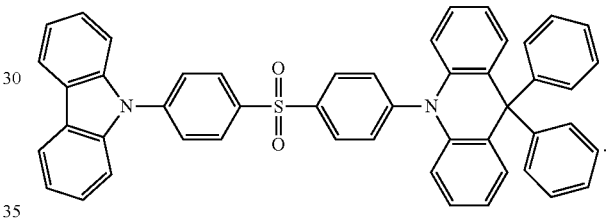

A synthesizing method of the thermally activated delayed fluorescent material includes:

In a step S10, 4-bromo-4'-iodo-diphenyl sulfone, a first reactant, and a first catalyst are added to a first container, and a first heat treatment is performed to obtain a first reaction solution.

The first container in this embodiment is a 100 ml two-necked bottle. Firstly, 4-bromo-4'-iodo-diphenyl sulfone (4.21 g, 10 mmol) and carbazole (1.67 g, 10 mmol) are separately added to the two openings. Then, cesium carbonate $CsCO_3$ (2.31 g, 12 mmol), cuprous iodide CuI (0.11 g, 0.6 mmol), and 18-crown-6 ether (52 mg, 0.2 mmol) are added to the first container. Then, the first container is vacuumed three times and nitrogen or an inert gas is introduced into the first container to prevent water and oxygen in the air from affecting the reaction. Then, 20 ml of N,N-dimethylpropenyl urea which oxygen is previously removed is added to the first container. Finally, the first container is heated to a temperature of 180° C., and the reactant is reacted at 180° C. for 24 hours. The reaction solution is cooled to room temperature to obtain the first reaction solution.

A chemical structural formula of 4-bromo-4'-iodo-diphenyl sulfone is as follows:

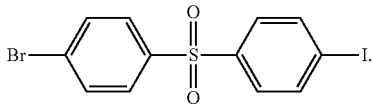

A chemical structural formula of carbazole is as follows:

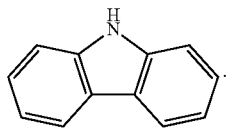 [SMILES: c1ccc2c(c1)[nH]c1ccccc12]

In a step S20, a separating treatment is performed on the first reaction solution to obtain a first intermediate.

First, the first reaction liquid is poured into 200 ml of ice water, and suction filtration is carried out to obtain a grayish-white solid. Then, the grayish-white solid is dissolved in dichloromethane and is spun to form a silica gel. Then, the silica gel is separated and purified by column chromatography. An eluting agent used in the column chromatography is a mixing solvent of dichloromethane and n-hexane with a volume ratio being 1:3. 3.3 g of the blue-white powder is obtained in a yield of 72%.

An ideal chemical formula of the first intermediate is 4-carbazole-4'-bromo-diphenyl sulfone having a following chemical structural formula as follows:

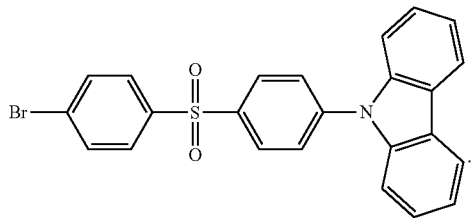 [SMILES: O=S(=O)(c1ccc(Br)cc1)c1ccc(-n2c3ccccc3c3ccccc32)cc1]

A chemical formula of the intermediate is $C_{24}H_{16}BrNO_2S$, which has eight different chemical environment hydrogens. A theoretical relative molecular mass is 462.36, and a theoretical mass content ratio of carbon, hydrogen, and nitrogen is: 62.35%: 3.49%: 3.03%.

Structural analysis, such as nuclear magnetic resonance, mass spectrometry, carbon spectrum, etc., are performed to the obtained blue-white powder as follows:

$^1$H NMR (300 MHz, $CD_2Cl_2$, δ): 8.55 (d, J=6.9 Hz, 2H), 8.19 (d, J=6.6 Hz, 2H), 7.90~7.74 (m, 4H), 7.58 (d, J=6.6 Hz, 2H), 7.58 (d, J=6.9 Hz, 2H), 7.3~57.16 (m, 4H).

A molecular weight of the compound obtained by the experiment is 462.27, and a mass content ratio of carbon, hydrogen, and nitrogen in the compound is: 62.31%: 3.47%: 3.00%.

From the analysis, it is found that the blue-white powder has a same chemical structural formula as the ideal first intermediate, i.e., the blue-white powder is the first intermediate.

In a step S30, the first intermediate, a second reactant, and a second catalyst are added to a second container, and a second heat treatment is performed to obtain a second reaction solution.

The second container in this embodiment is a 100 ml two-necked bottle. First, the first intermediate, i.e., 4-carbazole-4'-bromo-diphenyl sulfone (2.31 g, 5 mmol), the second reactant, i.e., 9,10-dihydro-9,9-diphenyl acridine (2.00 g, 6 mmol), palladium acetate (45 mg, 0.2 mmol), and tri-tert-butylphosphine tetrafluoroborate (0.17 g, 0.6 mmol) are added to the second container. Then, after the second container is placed in an argon-filled glove box, sodium tert-butoxide NaOt-Bu (0.58 g, 6 mmol) is added to the second container. Then, 40 ml of toluene which water and oxygen are previously removed is added to the second container. Further, the second container is heated to 110° C. for 24 hours. Finally, the second container is cooled to room temperature to obtain the second reaction solution.

9,10-dihydro-9,9-diphenyl acridine of the second reactant of has a chemical structural formula as follows:

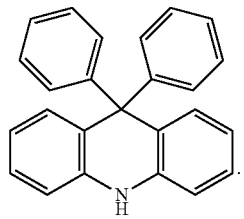 [SMILES: c1ccc(C2(c3ccccc3)c3ccccc3Nc3ccccc32)cc1]

In a step S40, the second reaction solution is treated to obtain the thermally activated delayed fluorescent agent.

First, the second reaction solution is added to 50 ml of ice water and extracted three times with dichloromethane to obtain an organic phase, and the organic phase is spun into a silica gel. Thereafter, solid-liquid separation was carried out by column chromatography. An eluting agent of the column chromatography including dichloromethane and n-hexane with a volume ratio being 1:5. 2.14 g of light blue powder is obtained in a yield of 60%. Finally, the light blue powder is purified using a sublimation instrument to obtain 1.3 g of product.

Nuclear magnetic resonance, carbon, mass spectrometry, and elemental analysis are performed to the product, and specific analysis is as follows:

$^1$H NMR (300 MHz, $CD_2Cl_2$, δ): 8.57 (d, J=6.6 Hz, 2H), 8.20 (d, J=6.0 Hz, 2H), 7.90-7.80 (m, 4H), 8.63 (d, J=6.3 Hz, 2H), 7.56 (d, J=6.9 Hz, 2H), 7.52-7.46 (m, 4H), 7.40 (d, J=6.0 Hz, 2H), 7.36-7.21 (m, 10H), 7.00-6.93 (m, 4H).

A chemical formula of the target product is $C_{49}H_{34}N_2O_2S$, a relative molecular mass is 714.88, and a relative molecular mass of the experimentally synthesized product is 714.67. A mass content ratio of carbon, hydrogen, and nitrogen in the target product is 82.33%: 4.79%: 3.92%. A mass content ratio of carbon, hydrogen, and nitrogen in the experimentally synthesized product is 82.17%: 4.63%: 3.74%.

From the analysis, it is found that the experimentally synthesized product is the same with the target product, that is, the 1.3 g of the product is the thermally activated delayed fluorescent material, and its chemical structural formula is:

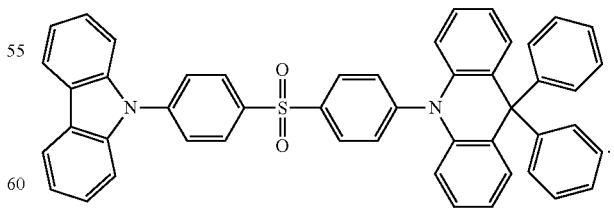

A theoretical simulation operation is performed on molecules of the thermally activated delayed fluorescent material in this embodiment. A lowest singlet state energy level is 2.88 eV, and a lowest triplet state energy level is 2.81 eV. A difference between the two levels is very small. The triplet state excitons can return to the singlet state through the reverse intersystem crossing, thereby achieving a quantum efficiency of 100%.

A photoluminescence spectrum of the thermally activated delayed fluorescent material in this embodiment at room temperature in a toluene solution shows that the wavelength is has a peak at about 430 nm, which illustrates that the thermally activated delayed fluorescent material in this embodiment can be used in a field of blue OLED.

Embodiment 2

A chemical structural formula of the thermally activated delayed fluorescent material in the present embodiment is:

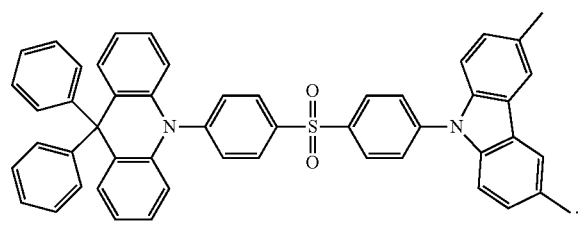 [SMILES: Cc1ccc2c(c1)c1cc(C)ccc1n2-c1ccc(S(=O)(=O)c2ccc(N3c4ccccc4C(c4ccccc4)(c4ccccc4)c4ccccc43)cc2)cc1]

A synthesizing method of the thermally activated delayed fluorescent material includes:

In a step S10, 4-bromo-4'-iodo-diphenyl sulfone, a first reactant, and a first catalyst are added to a first container, and a first heat treatment is performed to obtain a first reaction solution.

The first container in this embodiment is a 100 ml two-necked bottle. Firstly, 4-bromo-4'-iodo-diphenyl sulfone (4.21 g, 10 mmol) and 3,6-dimethylcarbazole (1.67 g, 10 mmol) are separately added to the two openings. Then, $CsCO_3$ (2.31 g, 12 mmol), CuI (0.11 g, 0.6 mmol), and 18-crown-6 ether (52 mg, 0.2 mmol) are added to the first container. Then, the first container is vacuumed three times and nitrogen or an inert gas is introduced into the first container to prevent water and oxygen in the air from affecting the reaction. Then, 20 ml of N,N-dimethylpropenyl urea which oxygen is previously removed is added to the first container. Finally, the first container is heated to a temperature of 180° C., and the reactant is reacted at 180° C. for 24 hours. The reaction solution is cooled to room temperature to obtain the first reaction solution.

A chemical structural formula of 4-bromo-4'-iodo-diphenyl sulfone is as follows:

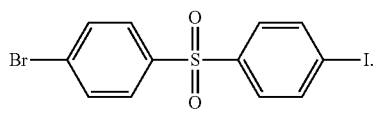

A chemical structural formula of 3,6-dimethylcarbazole is as follows:

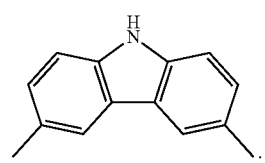

In a step S20, a separating treatment is performed on the first reaction solution to obtain a first intermediate.

First, the first reaction liquid is poured into 200 ml of ice water, and suction filtration is carried out to obtain a grayish-white solid. Then, the grayish-white solid is dissolved in dichloromethane and is spun to form a silica gel. Then, the silica gel is separated and purified by column chromatography. An eluting agent used in the column chromatography is a mixing solvent of dichloromethane and n-hexane with a volume ratio being 1:3. 3.2 g of the blue-white powder is obtained in a yield of 65%.

An ideal chemical formula of the first intermediate is 4-dimethylcarbazole-4'-bromo-diphenyl sulfone having a following chemical structural formula as follows:

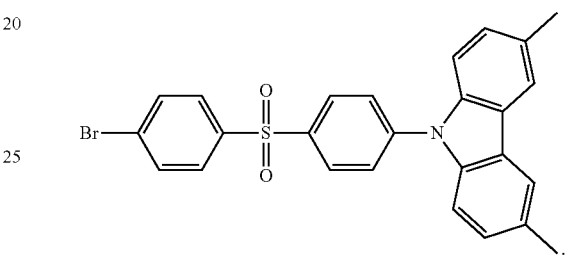

A chemical formula of the intermediate is $C_{26}H_{20}BrNO_2S$. A theoretical relative molecular mass is 489.04, and a theoretical mass content ratio of carbon, hydrogen, and nitrogen is: 63.68%: 4.11%: 2.86%.

Structural analysis, such as nuclear magnetic resonance, mass spectrometry, carbon spectrum, etc., are performed to the obtained blue-white powder as follows:

$^1$H NMR (300 MHz, $CD_2Cl_2$, δ): 8.80 (d, J=6.6 Hz, 2H), 7.89 (d, J=6.9 Hz, 2H), 7.65 (d, J=6.3 Hz, 2H), 7.53 (d, J=6.6 Hz, 2H), 7.36 (d, J=6.9 Hz, 2H), 6.96-6.90 (m, 4H), 2.48 (s, 6H).

A molecular weight of the compound obtained by the experiment is 489.00, and a mass content ratio of carbon, hydrogen, and nitrogen in the compound is: 63.90%: 4.17%: 2.91%.

From the analysis, it is found that the blue-white powder has a same chemical structural formula as the ideal first intermediate, i.e., the blue-white powder is the first intermediate.

In a step S30, the first intermediate, a second reactant, and a second catalyst are added to a second container, and a second heat treatment is performed to obtain a second reaction solution.

The second container in this embodiment is a 100 ml two-necked bottle. First, the first intermediate, i.e., 4-dimethylcarbazole-4'-bromo-diphenyl sulfone (2.45 g, 5 mmol), the second reactant, i.e., 9,10-dihydro-9,9-diphenyl acridine (2.00 g, 6 mmol), palladium acetate (45 mg, 0.2 mmol), and tri-tert-butylphosphine tetrafluoroborate (0.17 g, 0.6 mmol) are added to the second container. Then, after the second container is placed in an argon-filled glove box, sodium tert-butoxide NaOt-Bu (0.58 g, 6 mmol) is added to the second container. Then, 40 ml of toluene which water and oxygen are previously removed is added to the second container. Further, the second container is heated to 110° C. for 24 hours. Finally, the second container is cooled to room temperature to obtain the second reaction solution.

In a step S40, the second reaction solution is treated to obtain the thermally activated delayed fluorescent agent.

First, the second reaction solution is added to 50 ml of ice water and extracted three times with dichloromethane to obtain an organic phase, and the organic phase is spun into a silica gel. Thereafter, solid-liquid separation was carried out by column chromatography. An eluting agent of the column chromatography including dichloromethane and n-hexane with a volume ratio being 1:5. 2.08 g of light blue powder is obtained in a yield of 56%. Finally, the light blue powder is purified using a sublimation instrument to obtain 1.1 g of product.

Nuclear magnetic resonance, carbon, mass spectrometry, and elemental analysis are performed to the product, and specific analysis is as follows:

$^1$H NMR (300 MHz, CD$_2$Cl$_2$, δ): 8.76 (d, J=6.6 Hz, 2H), 8.13 (d, J=6.3 Hz, 2H), 7.93 (d, J=6.9 Hz, 2H), 7.64 (d, J=6.6 Hz, 2H), 7.53 (d, J=6.3 Hz, 2H), 7.42 (t, J=6.0 Hz, 4H), 7.36-7.08 (m, 14H), 6.96-6.84 (m, 4H), 2.45 (m, 6H).

A chemical formula of the target product is C$_{51}$H$_{38}$N$_2$O$_2$S, a relative molecular mass is 742.27, and a relative molecular mass of the experimentally synthesized product is 742.20. A mass content ratio of carbon, hydrogen, and nitrogen in the target product is 82.45%: 5.16%: 3.77%. A mass content ratio of carbon, hydrogen, and nitrogen in the experimentally synthesized product is 82.31%: 5.07%: 3.69%.

From the analysis, it is found that the experimentally synthesized product is the same with the target product, that is, the 1.1 g of the product is the thermally activated delayed fluorescent material, and its chemical structural formula is:

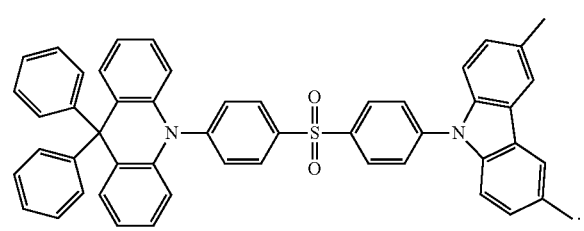 [SMILES: Cc1ccc2c(c1)c1cc(C)ccc1n2-c1ccc(S(=O)(=O)c2ccc(N3c4ccccc4C(c4ccccc4)(c4ccccc4)c4ccccc43)cc2)cc1]

A theoretical simulation operation is performed on molecules of the thermally activated delayed fluorescent material in this embodiment. A lowest singlet state energy level is 2.88 eV, and a lowest triplet state energy level is 2.81 eV. A difference between the two levels is very small. The triplet state excitons can return to the singlet state through the reverse intersystem crossing, thereby achieving a quantum efficiency of 100%.

A photoluminescence spectrum of the thermally activated delayed fluorescent material in this embodiment at room temperature in a toluene solution shows that the wavelength is has a peak at about 430 nm, which illustrates that the thermally activated delayed fluorescent material in this embodiment can be used in a field of blue OLED.

Embodiment 3

A chemical structural formula of the thermally activated delayed fluorescent material in the present embodiment is:

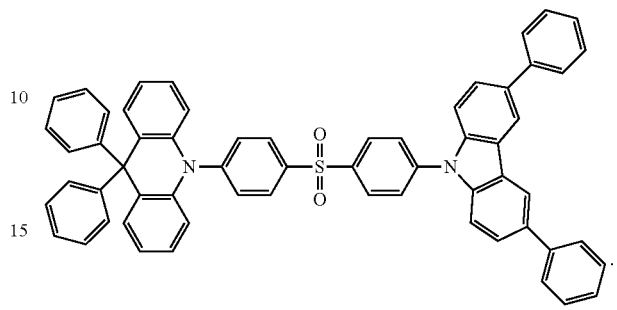

A synthesizing method of the thermally activated delayed fluorescent material includes:

In a step S10, 4-bromo-4'-iodo-diphenyl sulfone, a first reactant, and a first catalyst are added to a first container, and a first heat treatment is performed to obtain a first reaction solution.

The first container in this embodiment is a 100 ml two-necked bottle. Firstly, 4-bromo-4'-iodo-diphenyl sulfone (4.21 g, 10 mmol) and 3,6-diphenylcarbazole (3.19 g, 10 mmol) are separately added to the two openings. Then, CsCO$_3$ (2.31 g, 12 mmol), CuI (0.11 g, 0.6 mmol), and 18-crown-6 ether (52 mg, 0.2 mmol) are added to the first container. Then, the first container is vacuumed three times and nitrogen or an inert gas is introduced into the first container to prevent water and oxygen in the air from affecting the reaction. Then, 20 ml of N,N-dimethylpropenyl urea which oxygen is previously removed is added to the first container. Finally, the first container is heated to a temperature of 180° C., and the reactant is reacted at 180° C. for 24 hours. The reaction solution is cooled to room temperature to obtain the first reaction solution.

A chemical structural formula of 4-bromo-4'-iodo-diphenyl sulfone is as follows:

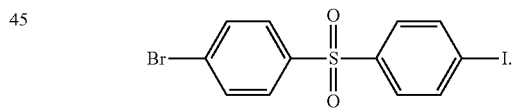

A chemical structural formula of 3,6-diphenylcarbazole is as follows:

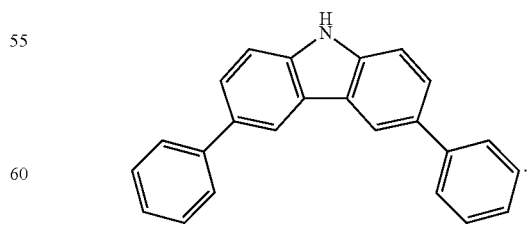

In a step S20, a separating treatment is performed on the first reaction solution to obtain a first intermediate.

First, the first reaction liquid is poured into 200 ml of ice water, and suction filtration is carried out to obtain a grayish-white solid. Then, the grayish-white solid is dissolved in dichloromethane and is spun to form a silica gel. Then, the silica gel is separated and purified by column chromatography. An eluting agent used in the column chromatography is a mixing solvent of dichloromethane and n-hexane with a volume ratio being 1:3. 4.1 g of the blue-white powder is obtained in a yield of 67%.

An ideal chemical formula of the first intermediate is 4-diphenylcarbazole-4'-bromo-diphenyl sulfone having a following chemical structural formula as follows:

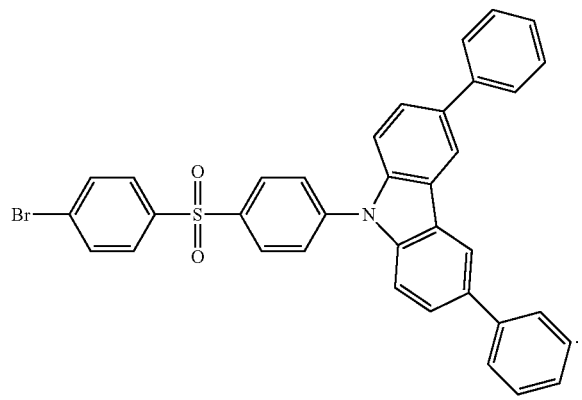 [SMILES: O=S(=O)(c1ccc(Br)cc1)c1ccc(-n2c3ccc(-c4ccccc4)cc3c3cc(-c4ccccc4)ccc32)cc1]

A chemical formula of the intermediate is $C_{36}H_{24}BrNO_2S$. A theoretical relative molecular mass is 613.07, and a theoretical mass content ratio of carbon, hydrogen, and nitrogen is: 70.36%: 3.94%: 2.28%.

Structural analysis, such as nuclear magnetic resonance, mass spectrometry, carbon spectrum, etc., are performed to the obtained blue-white powder as follows:

$^1$H NMR (300 MHz, $CD_2Cl_2$, δ): 8.30 (d, J=6.9 Hz, 2H), 8.13 (d, J=6.6 Hz, 2H), 7.90 (d, J=6.3 Hz, 2H), 7.75-7.65 (m, 6H), 7.57 (d, J=6.9 Hz, 2H), 7.49-7.41 (m, 10H).

A molecular weight of the compound obtained by the experiment is 613.01, and a mass content ratio of carbon, hydrogen, and nitrogen in the compound is: 70.21%: 3.81%: 2.11%.

From the analysis, it is found that the blue-white powder has a same chemical structural formula as the ideal first intermediate, i.e., the blue-white powder is the first intermediate.

In a step S30, the first intermediate, a second reactant, and a second catalyst are added to a second container, and a second heat treatment is performed to obtain a second reaction solution.

The second container in this embodiment is a 100 ml two-necked bottle. First, the first intermediate, i.e., 4-diphenylcarbazole-4'-bromo-diphenyl sulfone (3.07 g, 5 mmol), the second reactant, i.e., 9,10-dihydro-9,9-diphenyl acridine (2.00 g, 6 mmol), palladium acetate (45 mg, 0.2 mmol), and tri-tert-butylphosphine tetrafluoroborate (0.17 g, 0.6 mmol) are added to the second container. Then, after the second container is placed in an argon-filled glove box, sodium tert-butoxide NaOt-Bu (0.58 g, 6 mmol) is added to the second container. Then, 40 ml of toluene which water and oxygen are previously removed is added to the second container. Further, the second container is heated to 110° C. for 24 hours. Finally, the second container is cooled to room temperature to obtain the second reaction solution.

In a step S40, the second reaction solution is treated to obtain the thermally activated delayed fluorescent agent.

First, the second reaction solution is added to 50 ml of ice water and extracted three times with dichloromethane to obtain an organic phase, and the organic phase is spun into a silica gel. Thereafter, solid-liquid separation was carried out by column chromatography. An eluting agent of the column chromatography including dichloromethane and n-hexane with a volume ratio being 1:5. 1.95 g of light blue powder is obtained in a yield of 45%. Finally, the light blue powder is purified using a sublimation instrument to obtain 0.8 g of product, i.e., the thermally activated delayed fluorescent material.

A theoretical simulation operation is performed on molecules of the thermally activated delayed fluorescent material in this embodiment. A lowest singlet state energy level is 2.91 eV, and a lowest triplet state energy level is 2.85 eV. A difference between the two levels is very small. The triplet state excitons can return to the singlet state through the reverse intersystem crossing, thereby achieving a quantum efficiency of 100%.

A photoluminescence spectrum of the thermally activated delayed fluorescent material in this embodiment at room temperature in a toluene solution shows that the wavelength is has a peak at about 430 nm, which illustrates that the thermally activated delayed fluorescent material in this embodiment can be used in a field of blue OLED.

The present disclosure further provides an OLED light emitting device including a base substrate, an anode, a hole injection layer, a hole transport layer, a light-emitting layer, an electron transport layer, an electron injection layer, and a cathode.

The light-emitting layer is prepared by using the above thermally activated delayed fluorescent material or by using the material synthesized by the above synthesizing method.

The following description will be made in conjunction with specific embodiments.

Embodiment 4

Figure 2:
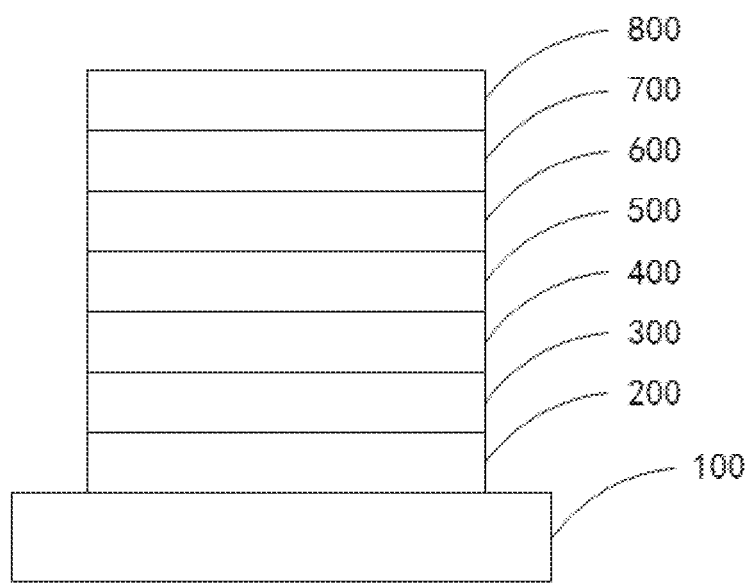
FIG. 2 is a structurally schematic diagram of an OLED light-emitting device of the present disclosure.

As shown in FIG. 2, an OLED light emitting device provided by the embodiment includes: a base substrate 100, an anode 200, a hole injection layer 300, a hole transport layer 400, a light-emitting layer 500, an electron transport layer 600, an electron injection layer 700, and a cathode 800.

The base substrate 100 includes a substrate, a thin film transistor layer, a source electrode, and a drain electrode. The base substrate is a glass substrate or can be a flexible substrate.

The anode 200 is prepared on a surface of the base substrate 100 using an ITO (indium tin oxide) material.

The hole injection layer 300 and the hole transport layer 400 are both prepared by using a poly 3,4-ethylenedioxythiophene:polystyrene sulfonate material.

A sum of thicknesses of the anode 200, the hole injection layer 300, and the hole transport layer 400 is 50 nm.

A material of the light-emitting layer 240 includes a host light-emitting material and a guest light-emitting material. The guest light-emitting material of the light-emitting layer 240 in this embodiment is prepared by using a thermally activated delayed fluorescent material synthesized by the synthesis method described in the Embodiment 1. A chemical structural formula is:

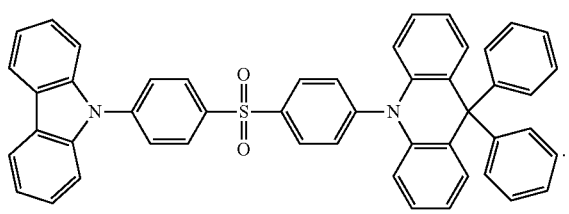 [SMILES: O=S(=O)(c1ccc(N2c3ccccc3C(c3ccccc3)(c3ccccc3)c3ccccc32)cc1)c1ccc(-n2c3ccccc3c3ccccc32)cc1]

The guest light-emitting material has a thickness of 40 nm.

The electron transport layer 600 is prepared using a 1,3,5-tris(3-(3-pyridyl)phenyl)benzene material.

The cathode 800 is prepared using an alloy of lithium fluoride and aluminum, and a thickness of the lithium fluoride film is 1 nm. A thickness of the aluminum film is 100 nm.

The OLED light-emitting device is measured by a Keithley source measuring system with a calibrated silicon photodiode and a French JY company SPEX CCD3000 spectrometer. The OLED light-emitting device has a maximum brightness of 1395 cd/m$^2$, a maximum current efficiency of 7.7 cd/A, and a CIE chromatogram y value is 0.09. When the y value is equal to zero, it is in blue. However, when the y value in this embodiment is close to zero, a maximum external quantum efficiency is 7.9%.

Embodiment 5

The OLED light-emitting device provided in this embodiment is different from the above-described fourth embodiment in that a guest luminescent material is different from a guest luminescent material of the fourth embodiment. Others are the same as in the fourth embodiment.

The guest luminescent material provided in this embodiment is prepared by using the thermal activation delayed fluorescent material synthesized by the synthesis method described in the Embodiment 2. A chemical structural formula is:

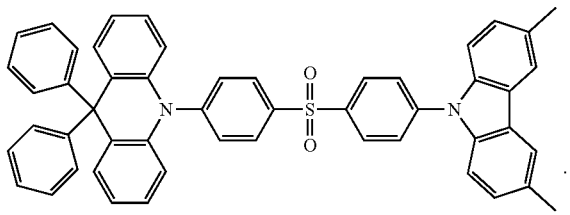 [SMILES: Cc1ccc2c(c1)c1cc(C)ccc1n2-c1ccc(S(=O)(=O)c2ccc(N3c4ccccc4C(c4ccccc4)(c4ccccc4)c4ccccc43)cc2)cc1]

A highest brightness of the OLED light-emitting device in this embodiment can reach 1057 cd/m2, the highest current efficiency can reach 7.6 cd/A, the CIE chromatogram y value is 0.09, and the maximum external quantum efficiency is 7.9%.

The OLED light-emitting device in this embodiment has a maximum brightness of 1057 cd/m$^2$, a maximum current efficiency of 7.6 cd/A, a CIE chromatogram y value is 0.09, and a maximum external quantum efficiency of 7.9%.

Embodiment 6

The OLED light-emitting device provided in this embodiment is different from the above-described fourth embodiment in that a guest luminescent material is different from a guest luminescent material of the fourth embodiment. Others are the same as in the fourth embodiment.

The guest luminescent material provided in this embodiment is prepared by using the thermal activation delayed fluorescent material synthesized by the synthesis method described in the Embodiment 3. A chemical structural formula is:

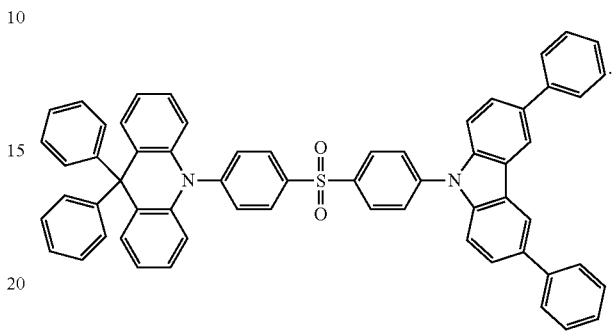

The OLED light-emitting device in this embodiment has a maximum brightness of 983 cd/m$^2$, a maximum current efficiency of 7.9 cd/A, a CIE chromatogram y value is 0.08, and a maximum external quantum efficiency of 7.9%.

Beneficial effects are that: the present disclosure synthesizes a thermally activated delayed fluorescent material with excellent luminescent properties by a combination of different functional groups, and improves a luminous efficiency of an OLED light-emitting device.

As described above, although the present disclosure has been described in preferred embodiments, they are not intended to limit the disclosure. One of ordinary skill in the art, without departing from the spirit and scope of the disclosure within, can make various modifications and variations, so the range of the scope of the disclosure is defined by the claims.

The invention claimed is:

1. A synthesizing method of a thermally activated delayed fluorescent material, the thermally activated delayed fluorescent material having a structural formula as follows:

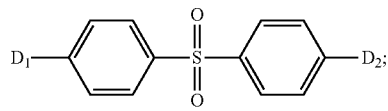

wherein $D_1$ is selected from one of following functional groups:

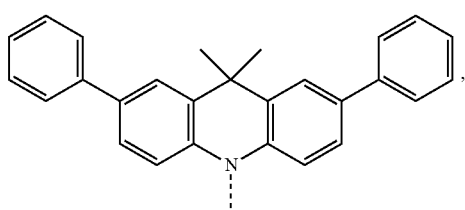

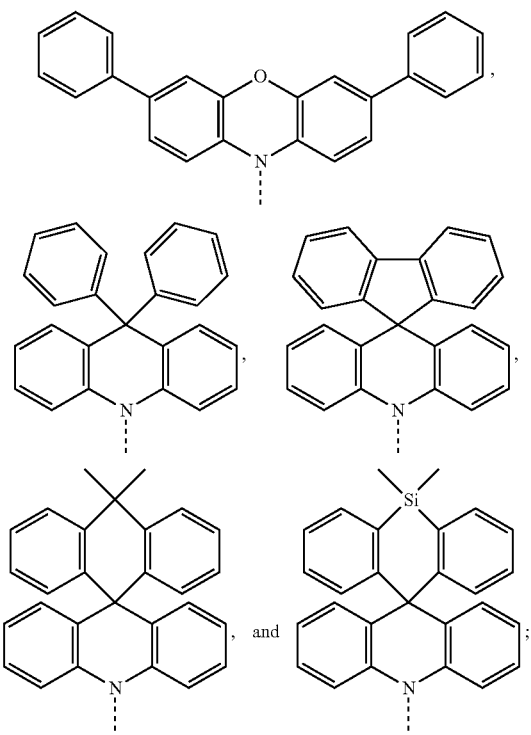

wherein D₂ is selected from one of following functional groups:

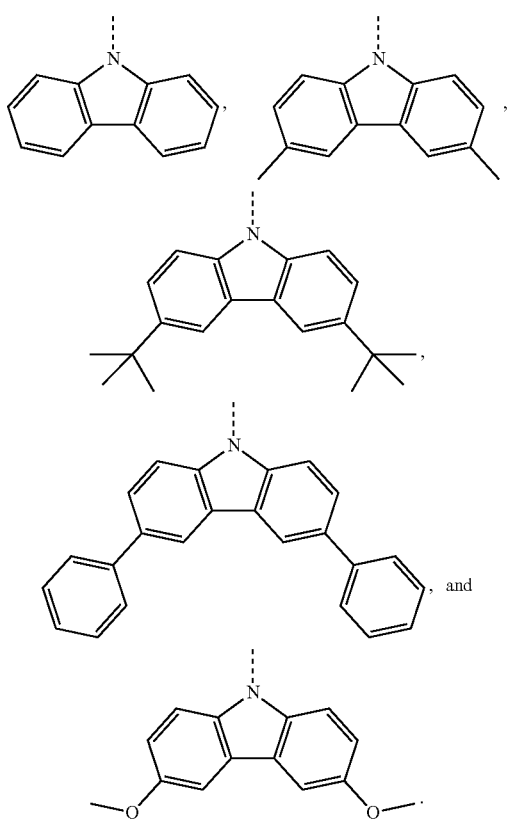

and the synthesizing method comprising:

a step S10 of adding 4-bromo-4'-iodo-diphenyl sulfone, a first reactant, and a first catalyst to a first container, and performing a first heat treatment to obtain a first reaction solution, wherein the first catalyst is a mixture of cesium carbonate, cuprous iodide, 18-crown-6 ether, and N,N'-dimethylpropylene urea;

a step S20 of performing a separating treatment on the first reaction solution to obtain a first intermediate;

a step S30 of adding the first intermediate, a second reactant, and a second catalyst to a second container, and performing a second heat treatment to obtain a second reaction solution, wherein the second catalyst is a mixture of palladium acetate, tri-tert-butylphosphine tetrafluoroborate, and toluene; and a step S40 of treating the second reaction solution to obtain the thermally activated delayed fluorescent agent.

2. The synthesizing method according to claim 1, wherein the first reactant is selected from one of following organic compounds:

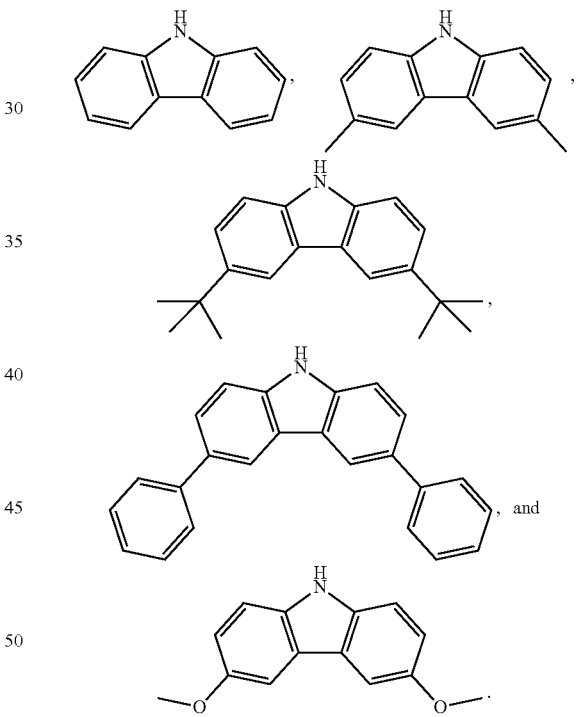

3. The synthesizing method according to claim 1, wherein the second reactant is selected from one of following organic compounds:

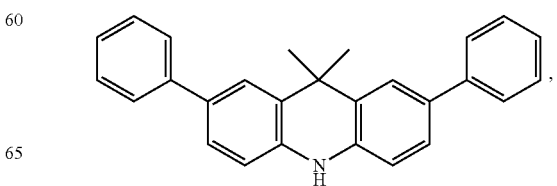

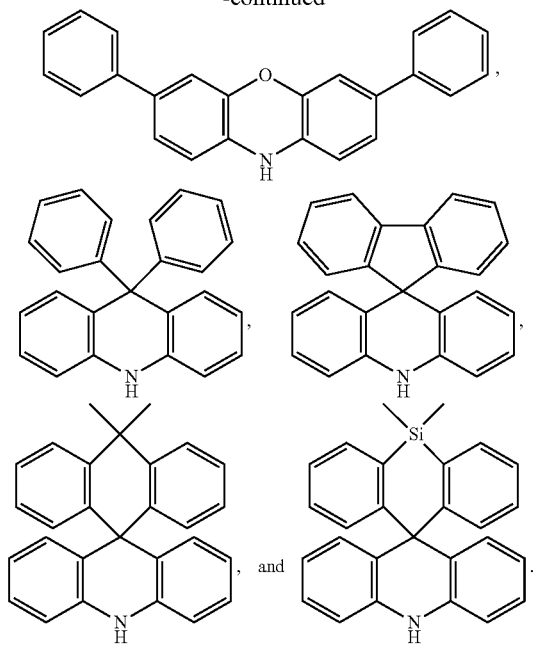

4. The synthesizing method according to claim 1, wherein the step S10 includes:

a step S101 of adding 4-bromo-4'-iodo-diphenyl sulfone, the first reactant, cesium carbonate, cuprous iodide, and 18-crown-6 ether to the first container;

a step S102 of vacuuming the first container three times and introducing nitrogen or an inert gas into the first container; and a step S103 of adding the N,N'-dimethylpropylene urea to the first container, and performing the first heat treatment to obtain the first reaction solution.

5. The synthesizing method according to claim 4, wherein a temperature of the first heat treatment is 180° C., and a time of the first heat treatment is 24 hours.

6. The synthesizing method according to claim 1, wherein the step S30 includes:

a step 301 of adding the first intermediate, the second reactant, palladium acetate, and tri-tert-butylphosphine tetrafluoroborate to the second container; and a step 302 of placing the second container in a glove box filled with nitrogen or an inert gas, adding sodium tert-butoxide, then adding the toluene to the second container, and performing the second heat treatment to obtain the second reaction solution.

7. The synthesizing method according to claim 6, wherein a temperature of the second heat treatment is 110° C., and a time of the second heat treatment is 24 hours.

8. A synthesizing method of a thermally activated delayed fluorescent material, the thermally activated delayed fluorescent material having a structural formula as follows:

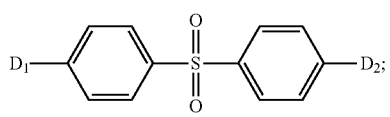

wherein $D_1$ is selected from one of following functional groups:

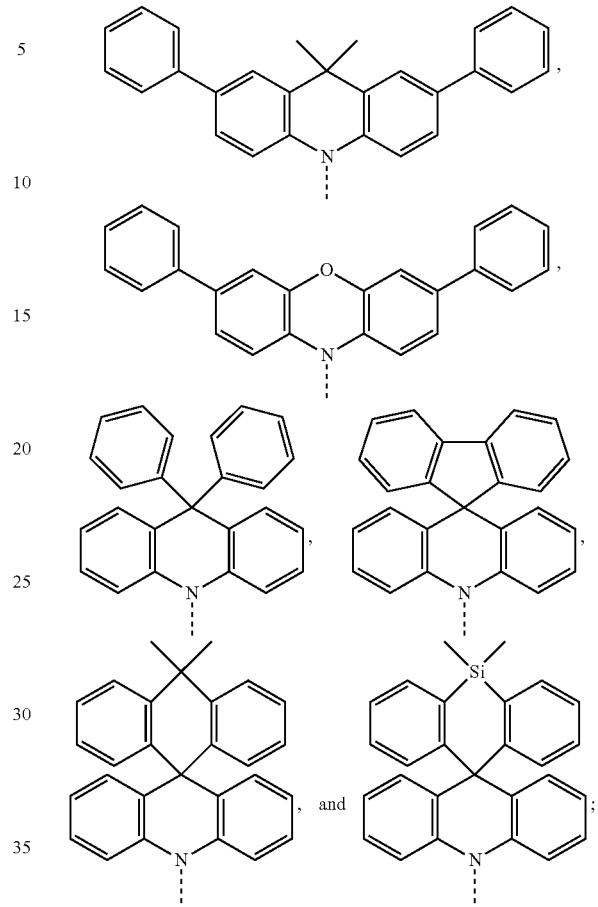

wherein $D_2$ is selected from one of following functional groups:

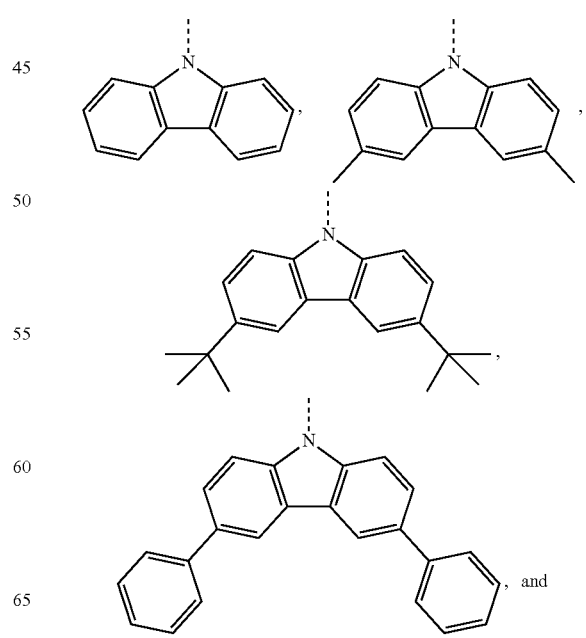

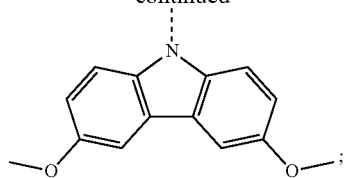

and the synthesizing method comprising:

a step S10 of adding 4-bromo-4'-iodo-diphenyl sulfone, a first reactant, and a first catalyst to a first container, and performing a first heat treatment to obtain a first reaction solution;

a step S20 of performing a separating treatment on the first reaction solution to obtain a first intermediate;

a step S30 of adding the first intermediate, a second reactant, and a second catalyst to a second container, and performing a second heat treatment to obtain a second reaction solution; and a step S40 of treating the second reaction solution to obtain the thermally activated delayed fluorescent agent.

9. The synthesizing method according to claim 8, wherein the first reactant is selected from one of following organic compounds:

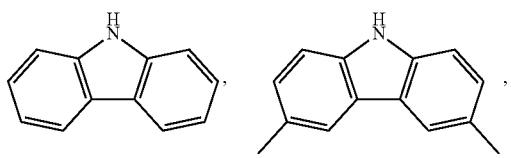

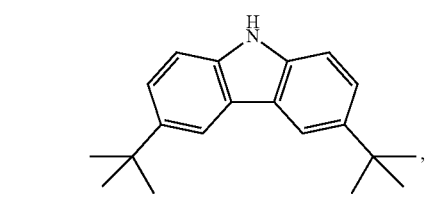

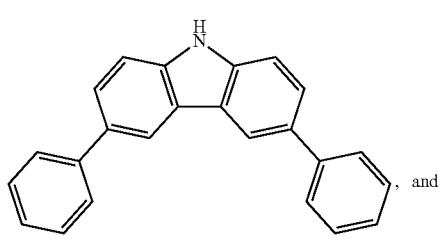

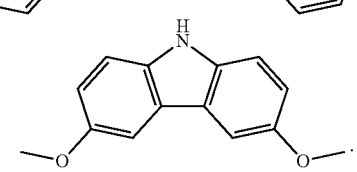

10. The synthesizing method according to claim 8, wherein the second reactant is selected from one of following organic compounds:

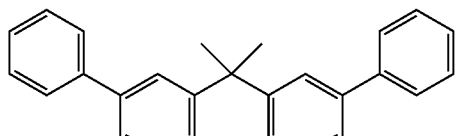

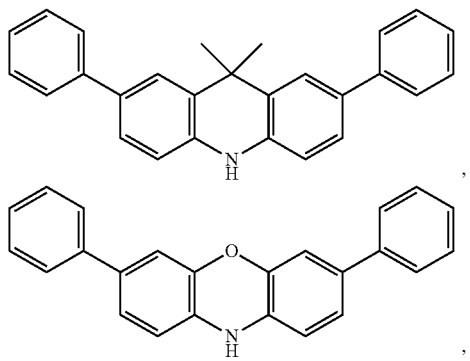

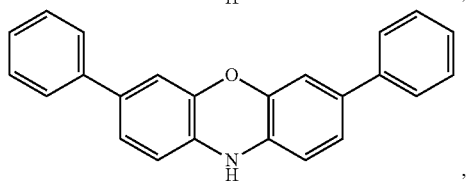

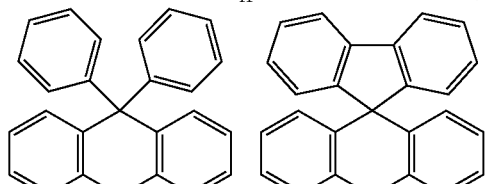

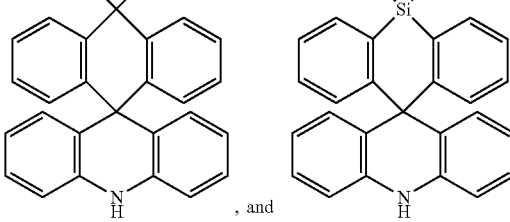

11. The synthesizing method according to claim 8, wherein the first catalyst is a mixture of cesium carbonate, cuprous iodide, 18-crown-6 ether, and N,N'-dimethylpropylene urea.

12. The synthesizing method according to claim 11, wherein the step S10 includes:

a step S101 of adding 4-bromo-4'-iodo-diphenyl sulfone, the first reactant, cesium carbonate, cuprous iodide, and 18-crown-6 ether to the first container;

a step S102 of vacuuming the first container three times and introducing nitrogen or an inert gas into the first container; and a step S103 of adding the N,N'-dimethylpropylene urea to the first container, and performing the first heat treatment to obtain the first reaction solution.

13. The synthesizing method according to claim 12, wherein a temperature of the first heat treatment is 180° C., and a time of the first heat treatment is 24 hours.

14. The synthesizing method according to claim 8, wherein the second catalyst is a mixture of palladium acetate, tri-tert-butylphosphine tetrafluoroborate, and toluene.

15. The synthesizing method according to claim 14, wherein the step S30 includes:

a step 301 of adding the first intermediate, the second reactant, palladium acetate, and tri-tert-butylphosphine tetrafluoroborate to the second container; and a step 302 of placing the second container in a glove box filled with nitrogen or an inert gas, adding sodium tert-butoxide, then adding the toluene to the second container, and performing the second heat treatment to obtain the second reaction solution.

16. The synthesizing method according to claim 15, wherein a temperature of the second heat treatment is 110° C., and a time of the second heat treatment is 24 hours.

* * * * *